(12) United States Patent
Ho et al.

(10) Patent No.: US 12,016,361 B2
(45) Date of Patent: *Jun. 25, 2024

(54) PROBIOTIC CULTURE AND USE THEREOF

(71) Applicant: GLAC BIOTECH CO., LTD., Tainan (TW)

(72) Inventors: Hsieh-Hsun Ho, Tainan (TW); Ching-Wei Chen, Tainan (TW); Yu-Fen Huang, Tainan (TW); Tsai-Hsuan Yi, Tainan (TW); Yi-Wei Kuo, Tainan (TW); Jia-Hung Lin, Tainan (TW); Shin-Yu Tsai, Tainan (TW)

(73) Assignee: GLAC BIOTECH CO., LTD., Tainan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/726,041

(22) Filed: Apr. 21, 2022

(65) Prior Publication Data

US 2023/0131386 A1 Apr. 27, 2023

(30) Foreign Application Priority Data

Oct. 26, 2021 (TW) ................................. 110139719

(51) Int. Cl.
| | | |
|---|---|---|
| *A23L 33/135* | (2016.01) | |
| *A61K 35/745* | (2015.01) | |
| *A61K 35/747* | (2015.01) | |
| *A61P 29/00* | (2006.01) | |
| *A61P 31/04* | (2006.01) | |

(52) U.S. Cl.
CPC .......... *A23L 33/135* (2016.08); *A61K 35/745* (2013.01); *A61K 35/747* (2013.01); *A61P 29/00* (2018.01); *A61P 31/04* (2018.01)

(58) Field of Classification Search
CPC ... A23L 33/135; A61K 35/745; A61K 35/747; A61P 29/00; A61P 31/04
See application file for complete search history.

(56) References Cited

U.S. PATENT DOCUMENTS

| | | | |
|---|---|---|---|
| 11,096,410 B2* | 8/2021 | Blanchard | A61K 31/702 |
| 2020/0390119 A1* | 12/2020 | Hsieh | A23C 9/1234 |
| 2021/0052676 A1* | 2/2021 | Hsieh | A61K 35/747 |

OTHER PUBLICATIONS

Ho et al. The Novel Use of Postbiotics of TYCA06/AP-32/CP-9 in the Amelioration of Atopic Dermatitis and Improvement of Skin Care—A Clinical Study, International Journal of Clinical and Diagnostic Research, Mar. 26, 2021, vol. 9, No. 1, 18-28 (Year: 2021).*
Ho et al. (The Novel Use of Postbiotics of TYCA06/AP-32/CP-9 in the Amelioration of Atopic Dermatitis and Improvement of Skin Care—A Clinical Study, International Journal of Clinical and Diagnostic Research, Mar. 26, 2021, vol. 9, No. 1, 18-28 (Year: 2021).*

* cited by examiner

Primary Examiner — Robert J Yamasaki
Assistant Examiner — Alexander M Duryee
(74) Attorney, Agent, or Firm — HSML P.C.

(57) ABSTRACT

A probiotic culture is prepared by cultivating a probiotic mixture in a collagen solution. The probiotic mixture includes *Lactobacillus acidophilus* TYCA06 deposited at the China General Microbiological Culture Collection Center (CGMCC) under an accession number CGMCC 15210, *Lactobacillus salivarius* subsp. *salicinius* AP-32 deposited at the China Center for Type Culture Collection (CCTCC) under an accession number CCTCC M 2011127, and *Bifidobacterium animalis* subsp. *lactis* CP-9 deposited at the CCTCC under an accession number CCTCC M 2014588, in a ratio of colony forming units which ranges from 1:0.125:0.125 to 1:8:8. Use of the probiotic culture for improving skin condition and for inhibiting pathogenic infection is also provided.

18 Claims, 7 Drawing Sheets

PROBIOTIC CULTURE AND USE THEREOF

CROSS-REFERENCE TO RELATED APPLICATION

This application claims priority of Taiwanese Invention Patent Application No. 110139719, filed on Oct. 26, 2021.

FIELD

The present disclosure relates to a probiotic culture prepared by cultivating a probiotic mixture in a collagen solution. The present disclosure also relates to use of the probiotic culture for improving a skin condition and for inhibiting pathogenic infection.

BACKGROUND

Skin is the largest protective barrier for the human body, and is able to prevent water loss, invasion of skin pathogens (such as Staphylococcus aureus, Propionibacterium acnes, etc.), and damages caused by various harmful environments. When skin is damaged, a variety of skin conditions might occur, including eczema, acne, melanogenesis, delay of wound healing, etc.

In recent years, the demand for skin care has been increasing, and in order to satisfy such great demand on the market, researchers in the pharmaceutical industry and the cosmetic industry endeavor to develop skin care products which can effectively improve various skin conditions.

Probiotics are live microorganisms that can improve the balance of intestinal microflora and regulate proper intestinal immunity, and have been widely used in food and health products. Examples of common probiotics include Lactobacillus spp., Lactococcus spp., Pediococcus spp., Streptococcus spp., Enterococcus spp., Bifidobacterium spp., Bacillus spp., Leuconostoc spp., etc.

Previous studies have reported applications of probiotic strains in skin care. For example, TW 202108125 A discloses a composition which has a skin-whitening effect and which contains fermentation products generated by at least one lactic acid bacterial strain selected from the group consisting of Bifidobacterium breve Bv-889, Bifidobacterium longum subsp. infantis BLI-02, Bifidobacterium animalis subsp. lactis CP-9, Bifidobacterium bifidum Bf-688, Lactobacillus salivarius subsp. salicinius AP-32, and Lactobacillus paracasei GL-156. The fermentation products of the aforesaid lactic acid bacterial strains, when used alone, were confirmed by experimentation to have the effect of inhibiting melanin production. However, such fermentation products were not found to improve other skin conditions.

Therefore, there is still a need for those skilled in the art to develop a new strategy that can be utilized for improving various skin conditions and inhibiting pathogenic infection.

SUMMARY

In a first aspect, the present disclosure provides a probiotic culture which can alleviate at least one of the drawbacks of the prior art. The probiotic culture is prepared by cultivating a probiotic mixture in a collagen solution. The probiotic mixture includes Lactobacillus acidophilus TYCA06 which is deposited at the China General Microbiological Culture Collection Center (CGMCC) under an accession number CGMCC 15210, Lactobacillus salivarius subsp. salicinius AP-32 which is deposited at the China Center for Type Culture Collection (CCTCC) under an accession number CCTCC M 2011127, and Bifidobacterium animalis subsp. lactis CP-9 which is deposited at the CCTCC under an accession number CCTCC M 2014588. A number ratio of Lactobacillus acidophilus TYCA06, to Lactobacillus salivarius subsp. salicinius AP-32, and to Bifidobacterium animalis subsp. lactis CP-9 ranges from 1:0.125:0.125 to 1:8:8.

In a second aspect, the present disclosure provides a method for improving a skin condition, which can alleviate at least one of the drawbacks of the prior art, and which includes administering to a subject in need thereof a composition including the aforesaid probiotic culture.

In a third aspect, the present disclosure provides a method for inhibiting pathogenic infection, which can alleviate at least one of the drawbacks of the prior art, and which includes administering to a subject in need thereof a composition including the aforesaid probiotic culture.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

Figure 1:
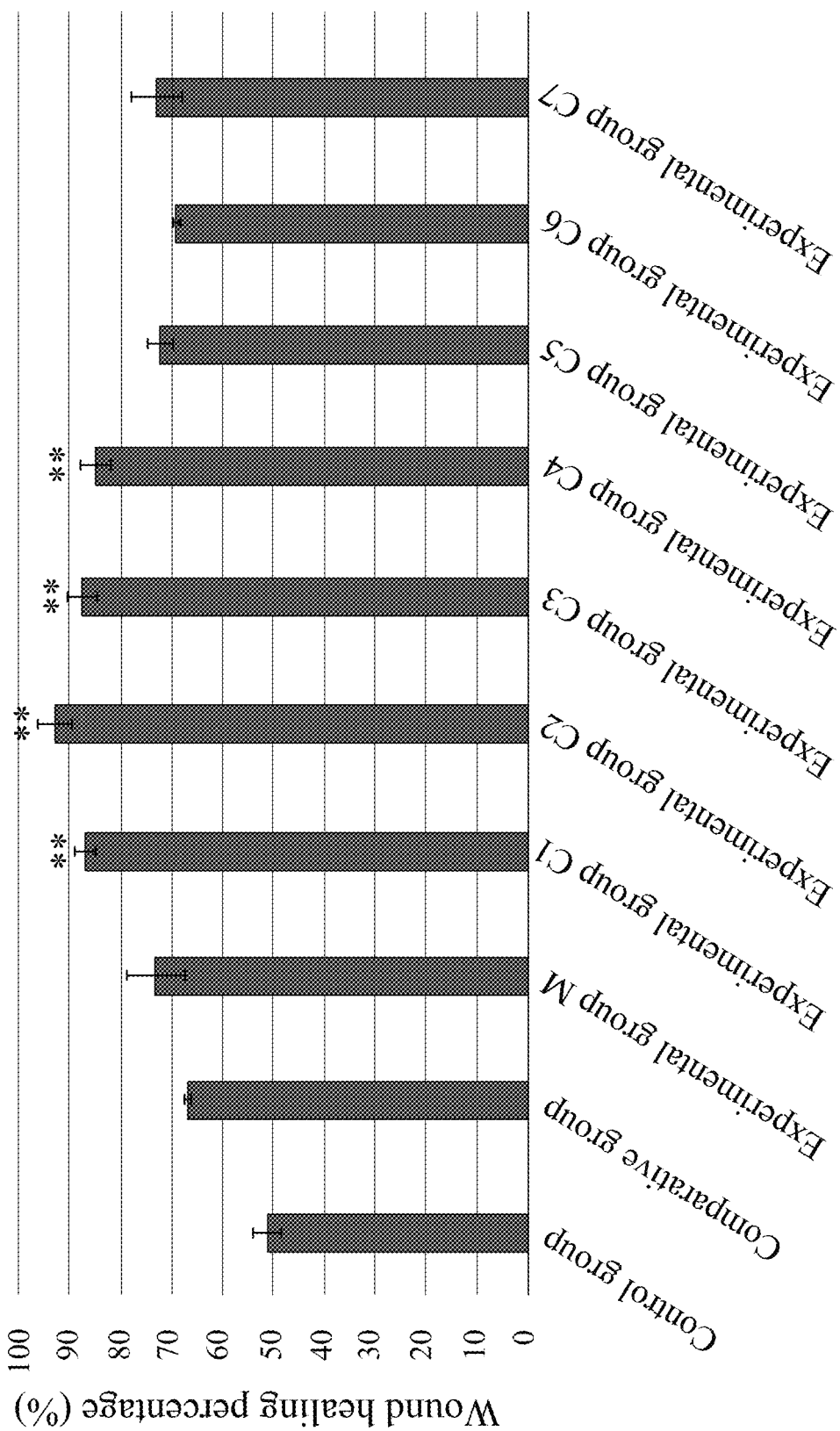
FIG. 1 shows the wound healing percentage of HaCaT cells in each group of Example 2, infra, in which the symbol "**" represents $p<0.01$ compared with the control group.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

In the development of a skin care product that is safe to be used for improving various skin-related conditions and inhibiting infections caused by skin pathogens, the applicant surprisingly found that a probiotic culture, which is obtained by cultivating, in a collagen solution, a mixture of three probiotic strains, i.e., *Lactobacillus acidophilus* TYCA06, to *Lactobacillus salivarius* subsp. *salicinius* AP-32, and to *Bifidobacterium animalis* subsp. *lactis* CP-9 in a number ratio ranging from 1:0.125:0.125 to 1:8:8, is capable of promoting wound healing, inhibiting melanogenesis, treating acne, reducing skin inflammation and skin brown spots, and exhibiting antibacterial activity against *Staphylococcus aureus* and *Propionibacterium acnes*. Hence, the probiotic culture, which is obtained by cultivating, in a collagen solution, the aforesaid probiotic strains in a specified range of number ratio thereof, is expected to be effective in improving various skin conditions and inhibiting pathogenic infection.

Therefore, the present disclosure provides a probiotic culture which is prepared by cultivating a probiotic mixture in a collagen solution. The probiotic mixture includes *Lactobacillus acidophilus* TYCA06 which is deposited at the China General Microbiological Culture Collection Center (CGMCC) under an accession number CGMCC 15210, *Lactobacillus salivarius* subsp. *salicinius* AP-32 which is deposited at the China Center for Type Culture Collection (CCTCC) under an accession number CCTCC M 2011127, and *Bifidobacterium animalis* subsp. *lactis* CP-9 which is deposited at the CCTCC under an accession number CCTCC M 2014588. A number ratio of *Lactobacillus acidophilus* TYCA06, to *Lactobacillus salivarius* subsp. *salicinius* AP-32, and to *Bifidobacterium animalis* subsp. *lactis* CP-9 in the probiotic mixture ranges from 1:0.125:0.125 to 1:8:8.

In certain embodiments, the number ratio of *Lactobacillus acidophilus* TYCA06, to *Lactobacillus salivarius* subsp. *salicinius* AP-32, and to *Bifidobacterium animalis* subsp. *lactis* CP-9 in the probiotic mixture ranges from 1:1:1 to 1:4:4. In an exemplary embodiment, the number ratio of *Lactobacillus acidophilus* TYCA06, to *Lactobacillus salivarius* subsp. *salicinius* AP-32, and to *Bifidobacterium animalis* subsp. *lactis* CP-9 in the probiotic mixture is 1:1:1.

According to the present disclosure, the probiotic mixture may have a bacterial concentration ranging from $1\times10^7$ CFU/mL to $1\times10^{12}$ CFU/mL. In an exemplary embodiment, the probiotic mixture has a bacterial concentration ranging from $1\times10^{10}$ CFU/mL to $1\times10^{10}$ CFU/mL.

According to the present disclosure, the collagen solution may be purchased commercially or self-prepared using standard techniques well known to those skilled in the art. For example, the collagen solution may be a natural product isolated from an animal tissue or a recombinant protein obtained by genetic engineering.

According to the present disclosure, the collagen solution may have a collagen concentration ranging from 10% (w/v, g/mL) to 50% (w/v, g/mL). In an exemplary embodiment, the collagen solution has a collagen concentration of 20% (w/v, g/mL).

As used herein, the term "cultivating" can be used interchangeably with other terms such as "fermentation" and "culturing".

It should be noted that the procedures and operating conditions for cultivating the probiotic mixture may be adjusted by those skilled in the art according to practical requirements.

According to the present disclosure, the cultivation of the probiotic mixture may be performed at a temperature ranging from 35° C. to 45° C. In an exemplary embodiment, the cultivation of the probiotic mixture is performed at a temperature of 37° C.

According to the present disclosure, the cultivation of the probiotic mixture may be performed for a time period ranging from 42 hours to 72 hours. In an exemplary embodiment, the cultivation of the probiotic mixture is performed for a time period of 48 hours.

According to the present disclosure, the probiotic culture may be subjected to a solid-liquid separation treatment, and hence may be substantially free of bacterial cells.

According to the present disclosure, the solid-liquid separation treatment may be selected from the group consisting of a centrifugation treatment, a filtration treatment, a concentration treatment, and combinations thereof. In an exemplary embodiment, the solid-liquid separation treatment is a centrifugation treatment.

According to the present disclosure, the probiotic culture may be subjected to a sterilization treatment, and hence may be substantially free of viable bacterial cells.

According to the present disclosure, the sterilization treatment may be performed at a temperature ranging from 90° C. to 180° C. for a time period ranging from 10 minutes to 30 minutes. In an exemplary embodiment, the sterilization treatment is performed at a temperature of 100° C. for a time period of 30 minutes.

As used herein, the term "substantially free of" means that the probiotic culture lacks a significant amount of a specified component (i.e., bacterial cells). In certain embodiments, the amount of the bacterial cells does not have a measurable effect on the properties of the probiotic culture. In other embodiments, the probiotic culture is completely free of bacterial cells.

According to the present disclosure, the probiotic culture may be further subjected to a drying treatment using techniques well-known to those skilled in the art after the solid-liquid separation treatment so as to be in a powder form. Examples of the drying treatment may include, but are not limited to, a freeze-drying treatment, a spray-drying treatment, a fluidized bed-drying treatment, and combinations thereof.

The present disclosure also provides a method for preparing a probiotic culture, which includes cultivating, in a collagen solution, a probiotic mixture including the aforesaid *Lactobacillus acidophilus* TYCA06, *Lactobacillus salivarius* subsp. *salicinius* AP-32, and *Bifidobacterium animalis* subsp. *lactis* CP-9. A number ratio of *Lactobacillus acidophilus* TYCA06, to *Lactobacillus salivarius* subsp. *salicinius* AP-32, and to *Bifidobacterium animalis* subsp. *lactis* CP-9 in the probiotic mixture ranges from 1:0.125:0.125 to 1:8:8. The procedures and conditions for preparing the collagen solution and for cultivating the probiotic mixture are as mentioned in the foregoing.

The present disclosure also provides a method for improving a skin condition, which includes administering to a subject in need thereof a composition including the aforesaid probiotic culture.

According to the present disclosure, the skin condition may be selected from the group consisting of wound, melanogenesis, acne, skin inflammation, skin brown spots, skin pathogen infection, and combinations thereof.

The present disclosure also provides a method for inhibiting pathogen infection, which includes administering to a subject in need thereof a composition including the aforesaid probiotic culture. In certain embodiments, the pathogen infection is caused by a skin pathogen.

As used herein, the term "inhibition" or "inhibiting" means stopping or slowing the growth of a pathogen in an infected subject.

According to the present disclosure, the pathogen infection may be caused by a pathogen selected from the group consisting of *Staphylococcus aureus, Propionibacterium acnes, Escherichia coli, Gardnerella vaginalis, Epidermophyton floccosum, Trichophyton rubrum*, and combinations thereof.

In an exemplary embodiment, the pathogen infection is caused by *Staphylococcus aureus*. In another exemplary embodiment, the pathogen infection is caused by *Propionibacterium acnes*.

According to the present disclosure, the composition may be formulated as a pharmaceutical composition. The pharmaceutical composition may further include a pharmaceutically acceptable carrier, and may be made into a dosage form suitable for oral administration using technology well-known to those skilled in the art.

Examples of the pharmaceutically acceptable carrier may include, but are not limited to, solvents, buffers, emulsifiers, suspending agents, decomposers, disintegrating agents, dispersing agents, binding agents, excipients, stabilizing agents, chelating agents, diluents, gelling agents, preservatives, wetting agents, lubricants, absorption delaying agents, liposomes, and the like. The choice and amount of the pharmaceutically acceptable carrier are within the expertise of those skilled in the art.

Examples of the dosage form for oral administration include, but are not limited to, sterile powder, tablets, troches, lozenges, pellets, capsules, dispersible powders or granules, solutions, suspensions, emulsions, drops, syrup, elixirs, slurry, and the like. In certain embodiments, the pharmaceutical composition is made into capsules suitable for oral administration.

As used herein, the term "administering" or "administration" means introducing, providing or delivering a predetermined active ingredient to a subject by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human.

According to the present disclosure, the dose and frequency of administration of the probiotic culture may vary depending on the following factors: the severity of the illness or disorder to be treated, routes of administration, and age, physical condition and response of the subject to be treated. In general, the probiotic culture may be orally administered in a single dose or in several doses.

According to the present disclosure, the composition may be formulated as a cosmeceutical composition. The cosmeceutical composition may further include the aforesaid pharmaceutically acceptable carrier and/or a cosmetically acceptable adjuvant, and may be made into an external preparation suitable for skincare or makeup using technology well-known to those skilled in the art.

Examples of the cosmetically acceptable adjuvant may include, but are not limited to, solvents, gelling agents, active agents, antioxidants, screening agents, surfactants, coloring agents, thickening agents, fillers, fragrances, and odor absorbers. The choice and amount of the cosmetically acceptable adjuvant are within the expertise of those skilled in the art.

Examples of the external preparation suitable for skincare or makeup include, but are not limited to, aqueous solutions, aqueous-alcohol solutions or oily solutions, oil-in-water types, water-in-oil types or complex emulsions, gels, ointments, creams, masks, patches, packs, bandages, liniments, powders, aerosols, sprays, lotions, serums, pastes, foams, dispersions, suspensions, drops, mousses, salves, sunblocks, tonic water, foundations, eyeshadows, makeup remover products, soaps, body cleansing products, and the like. In certain embodiments, the cosmeceutical composition is made into gels suitable for topical application to the skin.

The present disclosure will be further described by way of the following examples. However, it should be understood that the following examples are intended solely for the purpose of illustration and should not be construed as limiting the present disclosure in practice.

EXAMPLES

General Experimental Materials:
1. Probiotic Strains
A. *Lactobacillus acidophilus* TYCA06

*Lactobacillus acidophilus* TYCA06, which is disclosed in the applicant's patent TW 1701034 B and is known and readily available to the public, has been deposited at the Bioresource Collection and Research Center (BCRC) of the Food Industry Research and Development Institute (FIRDI) (No. 331, Shih-Pin Rd., Hsinchu City 300, Taiwan) under an accession number BCRC 910813 since Jan. 18, 2018, and has also been deposited at the China General Microbiological Culture Collection Center (CGMCC) of Chinese Academy of Sciences, the Institute of Microbiology (No. 1, West Beichen Rd., Chaoyang District, Beijing 100101, China), under an accession number CGMCC 15210 since Jan. 15, 2018 in accordance with the Budapest Treaty.

B. *Lactobacillus salivarius* Subsp. *Salicinius* AP-32

*Lactobacillus salivarius* subsp. *salicinius* AP-32, which is disclosed in the applicant's patents TW 1384990 B, TW 1709374 B, and CN 102835666 B, and which is known and readily available to the public, has been deposited at the BCRC of the FIRDI under an accession number BCRC 910437 since Jul. 30, 2009, and has also been deposited at the China Center for Type Culture Collection (CCTCC) of Wuhan University, the College of Life Sciences (No. 299, Bayi Rd., Wuchang District, Wuhan City 430072, Hubei Province, China) under an accession number CCTCC M 2011127 since Apr. 10, 2011 in accordance with the Budapest Treaty.

C. *Bifidobactorium animalis* subsp. *lactis* CP-9

*Bifidobacterium animalis* subsp. *lactis* CP-9, which is disclosed in the applicant's patents TW 1572713 B and CN 105985918 B, and which is known and readily available to the public, has been deposited at the BCRC of the FIRDI under an accession number BCRC 910645 since Aug. 21, 2014, and has also been deposited at the CCTCC of Wuhan University, the College of Life Sciences under an accession number CCTCC M 2014588 since Nov. 24, 2014 in accordance with the Budapest Treaty.

2. Pathogenic Bacterial Strains

The pathogenic bacterial strains used in the following experiments are readily available to the public, and were purchased from the BCRC of the FIRDI.

The relevant information regarding each of the pathogenic bacterial strains (including scientific name and BCRC accession number) is listed in Table 1 below.

TABLE 1

| Pathogenic bacterial strains | Accession number |
| --- | --- |
| Staphylococcus aureus | BCRC 12154 |
| Propionibacterium acnes | BCRC 16146 |

3. Collagen Solution

The collagen solution used in the following experiments was purchased from Hangzhou Nutrition Biotechnology Co., Ltd. (Product name: HNB® fish collagen peptide; Catalogue no.: C038A).

4. Source and Cultivation of Human Epidermal Keratinocyte Cell Line HaCaT and Mouse Skin Melanoma Cell Line B16F10

Human epidermal keratinocyte cell line HaCaT (from adult human skin) used in the following experiments was provided by Prof. Jiu-Yao Wang from the College of Medicine, National Cheng Kung University, Taiwan, while mouse skin melanoma cell line B16F10 was purchased from the BCRC of the FIRDI (under an accession number BCRC 60031).

The HaCaT cells and B16F10 cells were respectively incubated in 10-cm Petri dishes, each of which contained Gibco Dulbecco's modified Eagle's medium (DMEM) (Thermo Fisher Scientific) supplemented with 10% fetal bovine serum (FBS) (EMD Millipore Corp.) and 1% penicillin-streptomycin (Sigma-Aldrich). Subsequently, cultivation was conducted in an incubator with culture conditions set at 37° C. and 5% $CO_2$. Medium change was performed every 2 to 3 days. When reaching 80% to 90% of confluence, the cultured cells were subjected to sub-culturing.

General Procedures:

1. Statistical Analysis

All the experiments described below were performed in triplicates. The experimental data of all the test groups are expressed as mean±standard error of the mean (SEM), and were analyzed using two-tailed Student's t-test using GraphPad Prism 5 software (Developer: GraphPad Sofware, Inc., San Diego, CA), so as to assess the differences between the groups. Statistical significance is indicated by $p<0.05$.

Example 1. Preparation of Probiotic Culture Supernatant

First, a respective one of the probiotic strains described in section 1 of the General Experimental Materials was activated by inoculating into 5 mL of a Difco™ Lactobacilli MRS (De Man, Rogosa and Sharpe) broth (Manufacturer: BD; Catalogue no.: DF0881-17-5) supplemented with 0.05% (w/w) cysteine, and was then cultured at 37° C. for 24 hours to obtain an activated probiotic inoculum having a bacterial concentration that was adjusted to range from $1\times10^9$ CFU/mL to $1\times10^{10}$ CFU/mL, and that was determined using a plate counting medium. Next, the activated probiotic inoculums of Lactobacillus acidophilus TYCA06, Lactobacillus salivarius subsp. salicinius AP-32, and Bifidobacterium animalis subsp. lactis CP-9 were mixed at a specified number ratio shown in Table 2. The resultant probiotic inoculum mixture was inoculated at an amount of 3% (v/v) into 1 L of a collagen solution having a 20% collagen concentration (w/v; g/mL), and was then cultivated at 37° C. for 48 hours, thereby obtaining a three-probiotic culture in collagen, i.e., a corresponding one of three-probiotic cultures C1 to C7 as shown in Table 2.

TABLE 2

| Probiotic culture | Ratio of number of Lactobacillus acidophilus TYCA06, Lactobacillus salivarius subsp. salicinius AP-32, and Bifidobacterium, animalis subsp. lactis CP-9 |
| --- | --- |
| Three-probiotic culture C1 | 1:0.125:0.125 |
| Three-probiotic culture C2 | 1:1:1 |
| Three-probiotic culture C3 | 1:1:8 |
| Three-probiotic culture C4 | 1:8:1 |
| Three-probiotic culture C5 | 1:0.071:0.071 |
| Three-probiotic culture C6 | 1:1:14 |
| Three-probiotic culture C7 | 1:14:1 |

In addition, probiotic inoculums of Lactobacillus acidophilus TYCA06, Lactobacillus salivarius subsp. salicinius AP-32, and Bifidobacterium animalis subsp. lactis CP-9 were mixed at a number ratio of 1:1:1. The probiotic inoculum mixture thus obtained was inoculated at an amount of 3% (v/v) into 5 mL of a Difco™ Lactobacilli MRS broth, and was then cultivated at 37° C. for 48 hours, thereby obtaining a three-probiotic culture in MRS (abbreviated as three-probiotic culture M).

A respective one of the three-probiotic cultures C1 to C7 shown in Table 2 and the three-probiotic culture M was subjected to centrifugation at 4° C. under a speed of 3000 rpm for 10 minutes to form a three-probiotic culture supernatant and a pellet. Subsequently, the three-probiotic culture supernatant was collected, and was then subjected to a sterilization treatment by heating at 100° C. for 30 minutes. The resultant heat-sterilized three-probiotic culture supernatants (i.e., the three-probiotic culture supernatants C1 to C7 and the three-probiotic culture supernatant M respectively obtained from the three-probiotic cultures C1 to C7 and the three-probiotic culture M) were used in the following experiments.

Example 2. Evaluation for the Effect of Probiotic Culture Supernatant on Promotion of Wound Healing In order to evaluate the efficacy of the probiotic culture supernatant according to the present disclosure on promotion of wound healing, the following experiments were conducted.

Experimental Procedures:

First, the HaCaT cells described in section 4 of the General Experimental Materials were seeded at a concentration of $1\times10^6$ cells per well into wells of 6-well culture plates each containing 3 mL of DMEM supplemented with 10% FBS and 1% (v/v) penicillin-streptomycin, and then were divided into 10 groups, namely, a control group, a comparative group, and eight experimental groups (i.e., experimental groups C1 to C7 and experimental group M), followed by cultivation in an incubator with culture conditions set at 37° C. and 5% $CO_2$ for 24 hours.

Next, the cell culture of each group was scraped along the diameter of the corresponding well by using a pipette tip to create a cell-free wound area of approximately 5 μm. Then, the culture medium was removed, and the respective well was rinsed with phosphate-buffered saline (PBS). After adding a fresh culture medium (i.e., DMEM supplemented with 10% FBS and 1% (v/v) penicillin-streptomycin), each of the cell cultures of the experimental groups C1 to C7 and experimental group M was treated with an appropriate amount of a corresponding one of the three-probiotic culture supernatants C1 to C7 and the three-probiotic culture supernatant M prepared in Example 1, such that the final concentration of the three-probiotic culture supernatants C1 to C7 and the three-probiotic culture supernatant M in the corresponding experimental groups was 6.3 g/L. In addition, the cell culture of the comparative group was treated with an appropriate amount of a collagen solution such that the final concentration of collagen in the comparative group was 6.3 g/L, while the cell culture of the control group received no treatment.

Thereafter, the cell culture of each group was subjected to cultivation in an incubator with culture conditions set at 37° C. and 5% $CO_2$ for 24 hours. Before performing the cultivation and at the $24^{th}$ hour after start of the cultivation, the wound area in each group was observed under an inverted microscope (Manufacturer: Olympus Corporation; Model no.: CKX41) at a magnification of 100 and then photographed using a digital camera (Manufacturer: Canon Inc.; Model no.: PowerShot G15). Thereafter, digital images thus obtained were analyzed using ImageJ software (Developer: National Institutes of Health, USA) to calculate the size of wound area.

The wound healing percentage of the cell culture in a respective one of the control group, comparative group, experimental groups C1 to C7, and experimental group M was calculated by substituting the thus obtained size of wound area into the following formula (1):

$$A=[1-(B/C)]\times 100 \quad (1)$$

where A=wound healing percentage (%)
B=size of wound area at the $24^{th}$ hour after the start of cultivation
C=size of wound area before cultivation The data thus obtained were analyzed according to the procedure described in section 1 of the General Procedures.
Results:

FIG. 1 shows the wound healing percentage of HaCaT cells in each group. As shown in FIG. 1, in comparison with the control group, the wound healing percentages in the comparative group and the experimental group M showed no significant difference, while that of the experimental group C2 was significantly higher, suggesting that the three-probiotic culture supernatant C2 (which was prepared by cultivating, in a collagen solution, the probiotic inoculums of *Lactobacillus acidophilus* TYCA06, *Lactobacillus salivarius* subsp. *salicinius* AP-32, and *Bifidobacterium animalis* subsp. *lactis* CP-9 in a number ratio of 1:1:1) had an excellent effect in promotion of wound healing, and such effect was significantly better than that shown by the three-probiotic culture supernatant M (which was prepared by cultivating the aforesaid probiotic inoculums in the same number ratio in MRS broth), and that shown by the collagen solution. In addition, the experimental groups C1, C3 and C4 also demonstrated an excellent effect in promotion of wound healing similar to that shown by the experimental group C2; however, such effect was not observed in the experimental groups C5 to C7. This result indicates that the three-probiotic culture supernatants C1, C3 and C4, which were prepared by cultivating, in a collagen solution, the probiotic inoculums of *Lactobacillus acidophilus* TYCA06, *Lactobacillus salivarius* subsp. *salicinius* AP-32, and *Bifidobacterium animalis* subsp. *lactis* CP-9 in number ratios of 1:0.125:0.125, 1:1:8 and 1:8:1, respectively, are capable of exhibiting an excellent effect in promotion of wound healing.

Example 3. Evaluation for the Effect of Probiotic Culture Supernatant on Inhibition of Melanogenesis In order to evaluate the efficacy of the probiotic culture supernatant according to the present disclosure on inhibition of melanogenesis, the following experiments were conducted.
Experimental Procedures:

First, the B16F10 cells described in section 4 of the General Experimental Materials were seeded at a concentration of $2\times10^6$ cells per well into wells of 6-well culture plates each containing 3 mL of DMEM supplemented with 10% FBS and 1% (v/v) penicillin-streptomycin, and then were divided into 11 groups, namely, a normal control group, a pathological control group, a comparative group, and eight experimental groups (i.e., experimental groups C1 to C7 and experimental group M), followed by cultivation in an incubator with culture conditions set at 37° C. and 5% $CO_2$ for 24 hours.

Next, the culture medium in a respective one of the pathological control group, comparative group, experimental groups C1 to C7, and experimental group M was removed to be replaced with a fresh culture medium (i.e., DMEM supplemented with 10% FBS, 1% (v/v) penicillin-streptomycin, and 100 nM of α-melanocyte stimulating hormone (α-MSH)), followed by cultivation of the B16F10 cells in an incubator with culture conditions set at 37° C. and 5% $CO_2$ for 24 hours. Melanogenesis was thereby induced. In addition, the normal control group were also subjected to replacement of culture medium followed by cultivation as mentioned above, except that the fresh culture medium (DMEM) was not supplemented with α-MSH.

Thereafter, the culture medium in each group was removed to be replaced with a fresh culture medium (DMEM) supplemented with 10% FBS and 1% (v/v) penicillin-streptomycin but free from α-MSH, and then each of the cell cultures of the experimental groups C1 to C7 and experimental group M was treated with an appropriate amount of a corresponding one of the three-probiotic culture supernatants C1 to C7 and the three-probiotic culture supernatant M prepared in Example 1, such that the final concentration of the three-probiotic culture supernatants C1 to C7 and the three-probiotic culture supernatant M in the corresponding experimental groups was 6.3 g/L. In addition, the cell culture of the comparative group was treated with an appropriate amount of a collagen solution such that the final concentration of collagen in the comparative group was 6.3 g/L, while the cell cultures of the normal control group and the pathological control group received no treatment.

After cultivation in an incubator with culture conditions set at 37° C. and 5% $CO_2$ for 24 hours, the cell culture of each group was harvested and rinsed with PBS. Then, the cells in the respective group were added with 1 mL of a 1 N NaOH solution (diluted in water purified using reverse osmosis), and the resultant mixture was subjected to a heating treatment at 80° C. for 1 hour, followed by a centrifugation treatment under a speed of 3000 rpm for 3 minutes to form supernatant and pellet fractions. Subsequently, 100 μL of the supernatant was collected and was then subjected to light absorbance measurement at a wavelength of 405 nm ($OD_{405}$) using an ELISA microplate reader (Manufacturer: BioTek Instruments, Inc.; Model No: μQuant™).

Figure 2:
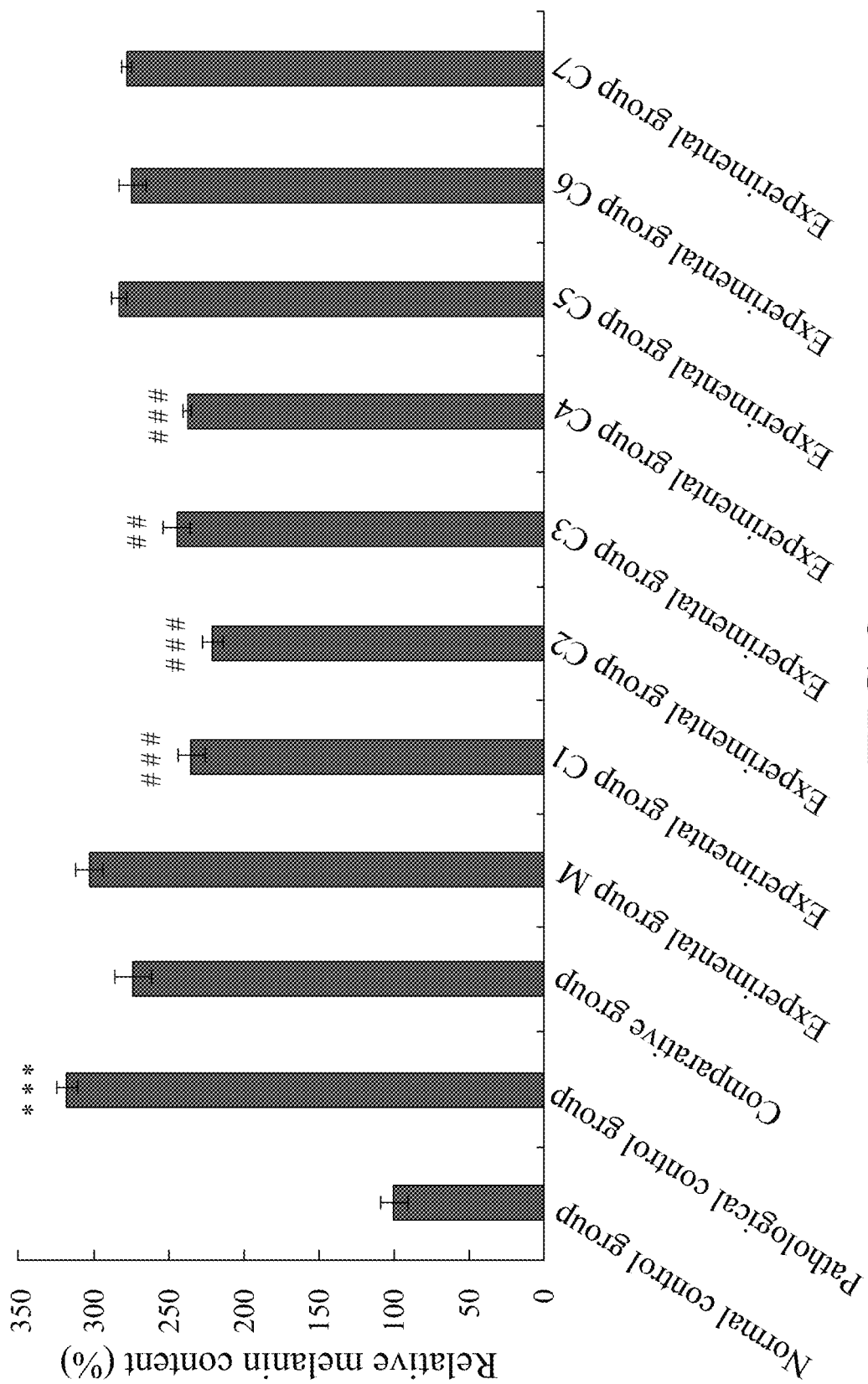
FIG. 2 shows the relative amount of melanin in B16F10 cells in each group of Example 3, infra, in which the symbol "***" represents $p<0.001$ compared with the normal control group, the symbol "##" represents $p<0.01$ compared with the pathological control group, and the symbol "###" represents $p<0.001$ compared with the pathological control group.

The relative melanin content in the cell culture of a respective one of the normal control group, pathological control group, comparative group, experimental groups C1 to C7, and experimental group M was calculated using the following formula (2):

$$D=(E/F)\times 100 \quad (2)$$

where D=relative melanin content (%)
  E=$OD_{405}$ of respective group
  F=$OD_{405}$ of normal control group The data thus obtained were analyzed according to the procedure described in section 1 of the General Procedures.
Results:

FIG. 2 shows the relative melanin content in the B16F10 cells of each group. As shown in FIG. 2, the relative melanin content in the normal control group was significantly lower than that of the pathological control group, indicating that α-MSH successfully induced melanogenesis (i.e., production of melanin) in the B16F10 cells. In comparison with the pathological control group, the relative melanin contents in the comparative group and the experimental group M showed no significant difference, while that of the experimental group C2 was significantly lower. This result suggests that the three-probiotic culture supernatant C2 (which was prepared by cultivating, in a collagen solution, the probiotic inoculums of Lactobacillus acidophilus TYCA06, Lactobacillus salivarius subsp. salicinius AP-32, and Bifidobacterium animalis subsp. lactis CP-9 in a number ratio of 1:1:1) had an excellent inhibitory effect on melanogenesis in B16F10 cells cultivated in the presence of α-MSH, and such effect was significantly better than that shown by the three-probiotic culture supernatant M (which was prepared by cultivating the aforesaid probiotic inoculums in the same number ratio in MRS broth) and that shown by the collagen solution.

In addition, the experimental groups C1, C3 and C4 also demonstrated an excellent effect in inhibition of melanogenesis similar to that shown by the experimental group C2; however, such effect was not observed in the experimental groups C5 to C7. This result indicates that the three-probiotic culture supernatants C1, C3 and C4 (which were prepared by cultivating, in a collagen solution, the probiotic inoculums of Lactobacillus acidophilus TYCA06, Lactobacillus salivarius subsp. salicinius AP-32, and Bifidobacterium animalis subsp. lactis CP-9 in number ratios of 1:0.125:0.125, 1:1:8 and 1:8:1, respectively) are capable of exhibiting an excellent effect in inhibition of melanogenesis, and hence, is expected to achieve skin whitening effect.

Example 4. Evaluation for Antibacterial Effect of Probiotic Culture Supernatant

In order to evaluate the effect of the probiotic culture supernatant according to the present disclosure against skin pathogens, the following experiments were conducted.
Experimental Procedures:
A. Determination of Antibacterial Activity Against Staphylococcus aureus First, Staphylococcus aureus described in section 2 of the General Experimental Materials was activated by inoculating into a nutrient broth (Manufacturer: HiMedia Laboratories Pvt. Ltd., India; Catalogue no.: M002), and was then cultured at 37° C. for 20 hours. The resultant bacterial inoculum was divided into 4 groups, namely, a normal control group, a comparative group, and two experimental groups (i.e., experimental group M and experimental group C), each having a volume of 100 μL and a bacterial concentration that was adjusted to $1\times 10^{9}$ CFU/mL, and that was determined using a plate counting medium. Next, each of the bacterial inoculums of the experimental groups M and C was treated with 4.9 mL of a corresponding one of the three-probiotic culture supernatant M and the three-probiotic culture supernatant C2 prepared in Example 1. In addition, the bacterial inoculum of the comparative group was treated with 4.9 mL of a collagen solution, while the bacterial inoculum of the normal control group received no treatment.

After cultivation at 37° C. for 6 hours, the resultant bacterial culture was subjected to ten-fold serial dilution, so as to obtain diluted bacterial cultures prepared using a dilution factor ranging from $10^{1}$ to $10^{3}$. Then, 100 μL of a respective one of the diluted bacterial cultures was evenly spread on a nutrient agar plate, followed by cultivation at 37° C. for 48 hours. Subsequently, the number of bacterial colonies formed on the nutrient agar plate of each group was calculated, and the bacterial number in the bacterial culture of each group was determined according to the dilution factor.

Figure 3:
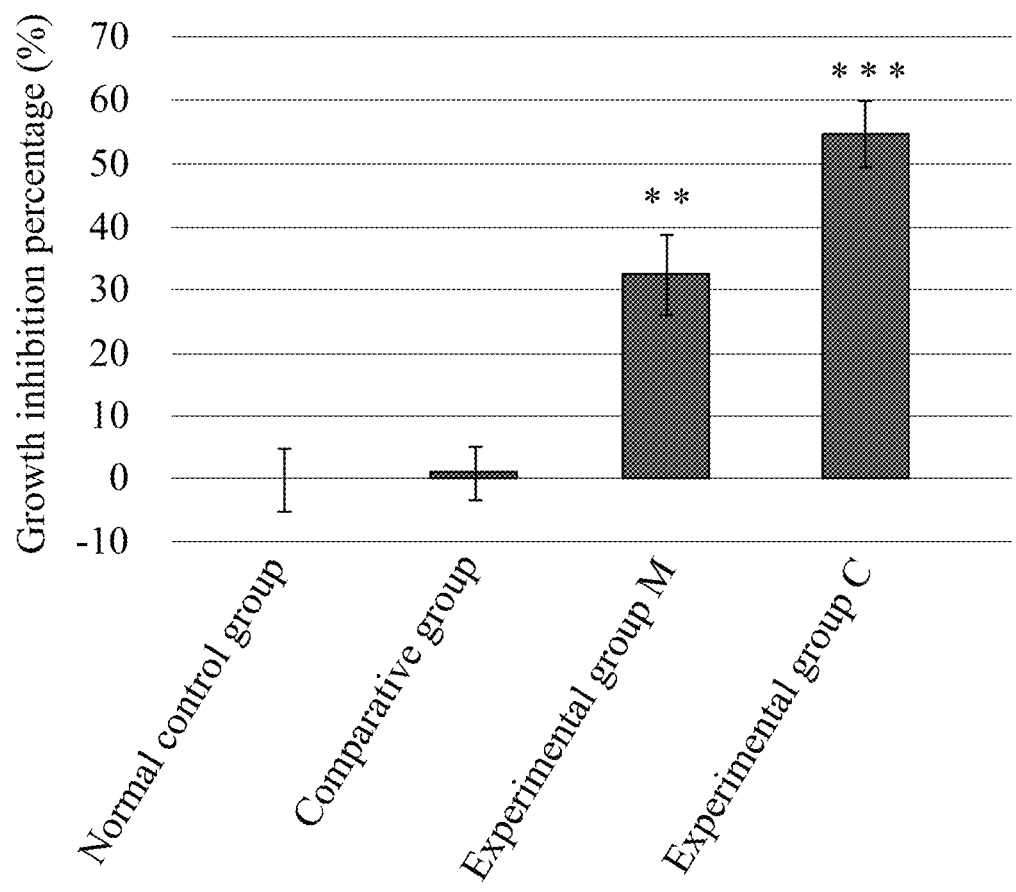
FIG. 3 shows the growth inhibition percentage of Staphylococcus aureus in each group of Example 4, infra, in which the symbols "" and "*" respectively represent $p<0.01$ and $p<0.001$ compared with the normal control group.

The percentage of growth inhibition of Staphylococcus aureus in a respective one of the normal control group, comparative group, experimental group M, and experimental group C was calculated by substituting the thus determined bacterial number into the following formula (3):

$$G=[1-(H/I)]\times 100 \quad (3)$$

where G=growth inhibition percentage (%)
  H=bacterial number of respective group
  I=bacterial number of the normal control group The data thus obtained were analyzed according to the procedure described in section 1 of the General Procedures, and the results are shown in FIG. 3.
B. Determination of Antibacterial Activity Against Propionibacterium acnes Propionibacterium acnes described in section 2 of the General Experimental Materials was activated by inoculating into a tryptone soy broth (Manufacturer: HiMedia Laboratories Pvt. Ltd., India; Catalogue no.: 211825) supplemented with 5% of defibrinated sheep blood, and was then cultured at 37° C. for 48 hours. The resultant bacterial inoculum of Propionibacterium acnes was divided into 4 groups similar to those of the bacterial inoculum of Staphylococcus aureus (see section A of this example), each of which was then subjected to the aforesaid treatment with the corresponding three-probiotic culture supernatant or the collagen solution or received no treatment. Ten-fold serial dilution as described for Staphylococcus aureus was then conducted, so as to obtain diluted bacterial cultures having a dilution factor ranging from $10^{1}$ to $10^{3}$. Then, 100 μL of a respective one of the diluted bacterial cultures of Propionibacterium acnes was evenly spread on a nutrient agar plate, followed by cultivation using the procedures described in section A of this example. The number of bacterial colonies formed on the nutrient agar plate of each group was calculated, and the bacterial number in the bacterial culture of each group was determined according to the dilution factor.

The percentage of growth inhibition of Propionibacterium acnes in a respective one of the normal control group, comparative group, experimental group M, and experimental group C was calculated by using the aforesaid formula (3).

Figure 4:
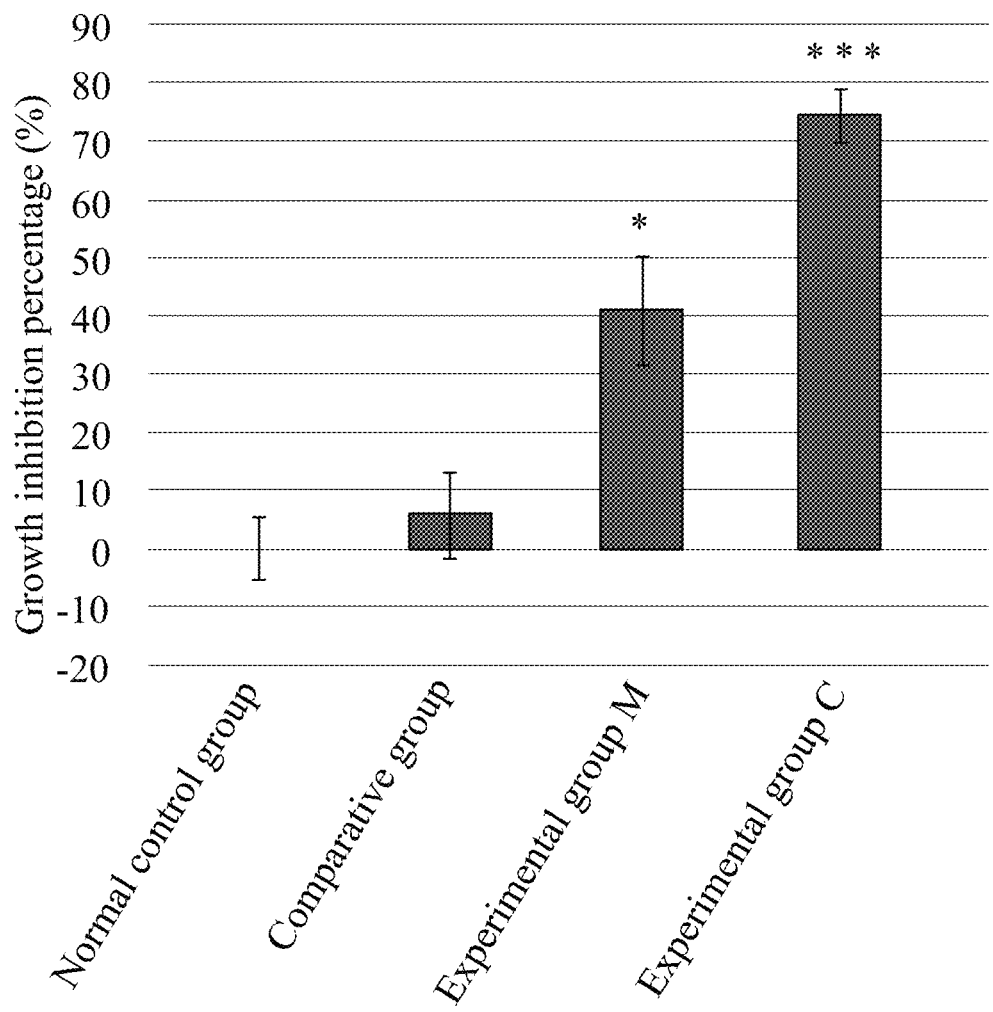
FIG. 4 shows the growth inhibition percentage of Propionibacterium acnes in each group of Example 4, infra, in which the symbols "*" and "***" respectively represent $p<0.05$ and $p<0.001$ compared with the normal control group.

The data thus obtained were analyzed according to the procedure described in section 1 of the General Procedures, and the results are shown in FIG. 4.

Results:

FIGS. 3 and 4 respectively show the growth inhibition percentages of *Staphylococcus aureus* and *Propionibacterium acnes* in each group. As shown in FIGS. 3 and 4, the growth inhibition percentages of *Staphylococcus aureus* and *Propionibacterium acnes* in the experimental group C were significantly respectively higher than those in the experimental group M, while those in the comparative group showed no significant difference when compared with those in the normal control group.

This results indicate that: collagen itself has no antibacterial activity; however, the three-probiotic culture supernatant C2, which was prepared by cultivating, in a collagen solution, the probiotic inoculums of *Lactobacillus acidophilus* TYCA06, *Lactobacillus salivarius* subsp. *salicinius* AP-32, and *Bifidobacterium animalis* subsp. *lactis* CP-9 in a number ratio of 1:1:1, is capable of exhibiting a significantly enhanced antibacterial activity.

Example 5. Evaluation for the Effect of Probiotic Culture Supernatant on Improvement of Skin Condition In order to evaluate the efficacy of the probiotic culture supernatant according to the present disclosure on improvement of various skin conditions, the following experiments were conducted.

Experimental Subjects:

20 test subjects (including 8 male subjects and 12 female subjects aged between 18 and 50 years old) participating in the following experiments were enrolled using procedures approved by the ethics committee of the Antai Medical Care Corporation Antai Tian-Sheng Memorial Hospital, Pingtung, Taiwan. In addition, a written informed consent was obtained from each of the test subjects.

Experimental Materials:

1. Preparation of Test Gels

An experimental gel and a control gel, which were used in the following experiments and which can be applied onto human skin, were prepared using the recipe shown in Table 3 below.

TABLE 3

| Ingredient | Experimental gel Amount (%) (w/w) | Control gel Amount (%) (w/w) |
| --- | --- | --- |
| Three-probiotic culture supernatant C2 | 5 | 0 |
| Carbomer (Carbopol ® 940 polymer available from Lubrizol Corp., USA) | 0.3 | 0.3 |
| Ammonium acryloyldimethyltaurate/VP copolymer (Aristoflex ® AVC available from Clariant AG, Switzerland) | 0.7 | 0.7 |
| Sodium hyaluronate (Hybloom ™ HA-THM available from Bloomage BioTechnology Corp. Ltd., China) | 0.01 | 0.01 |
| Water | 93.99 | 98.99 |

The experimental gel was prepared according to the following procedure. First, powders of carbomer, ammonium acryloyldimethyltaurate/VP copolymer, and sodium hyalorunate were added into water to generate swelling, and the resultant first mixture was placed in a blender to be stirred until the first mixture became gelatinous. Next, the three-probiotic culture supernatant C2 prepared in Example 1 was added to form a second mixture, followed by adjusting the pH of the second mixture to a range from 5.0 to 5.5 using an aqueous sodium hydroxide solution.

In addition, the control gel was prepared for comparison purpose using procedure that is substantially similar to that of the experimental gel, except that the three-probiotic culture supernatant C2 was not added.

A. Administration of Gel

The skin on the right face and the skin on the left face of each test subject, which respectively served as an experimental area and a control area, were respectively topically administered with the experimental gel and the control gel prepared in section 1 of the Experimental Materials. A respective one of the experimental area and the control area was subjected to the following dosing regimen: 3 mg to 5 mg of the gel was administered per 1 $cm^2$ area twice daily for a total of 28 days.

B. Morphological Observation of Acne

Before administration of the gel (i.e., on day 0), and on the $14^{th}$ and $28^{th}$ days after start of administration of the gel (i.e., days 14 and 28), 10 test subjects having similar acne symptoms on the right face and left face were selected from the 20 test subjects, and were then subjected to observation of acne on the skin of the experimental and control areas. To be specific, for each test subject, sites of acne on the skin of the experimental area administered with the experimental gel and those on the skin of the control area administered with the control gel were observed, and were then photographed using Intelligent Skin Analysis System (Manufacturer: Beijing Yi Li Mei Technology Co., Ltd., China; Model no.: ES3100).

Figure 5:
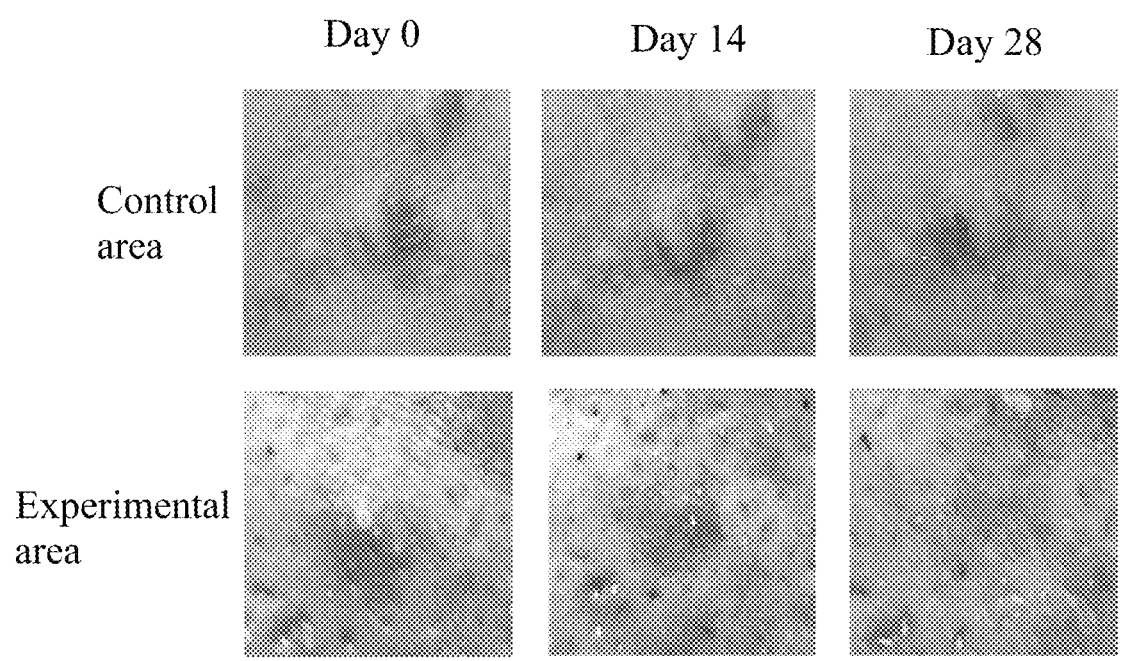
FIG. 5 shows the morphological observation result of acne in the experimental area and control area of Example 5, infra.

FIG. 5 shows the morphological observation result of acne on the skin in the experimental area administered with the experimental gel and in the control area administered with the control gel, before administration (i.e., on day 0) and on days 14 and 28 after start of administration. As shown in FIG. 5, on day 14 after start of administration, the redness and swelling at sites of acne on the skin in the experimental area administered with the experimental gel were significantly improved, and on day 28 after start of administration, the redness and swelling at sites of acne on the skin in the experimental area were completely eliminated with barely any scar remaining. In contrast, the redness and swelling at sites of acne on the skin in the control area administered with the control gel did not show significant improvement over a time period from day 0 to day 28 after start of administration.

C. Determination of Relative Skin Inflammation Index

Before administration of the gel (i.e., on day 0), and on the $28^{th}$ day after start of administration of the gel (i.e., day 28), for each test subject, the skin of the experimental area administered with the experimental gel and the skin of the control area administered with the control gel were subjected to measurement of skin inflammation index using VISIA™ Complexion Analysis (Manufacturer: Canfield Scientific, Inc., USA).

The relative skin inflammation index was calculated by substituting the number of reddened parts on the skin of the respective one of the experimental and control areas on day 0 and on the $28^{th}$ day after start of administration of the gel into the following formula (4):

$$J = (K/L) \times 100 \qquad (4)$$

where J=relative skin inflammation index (%)
K=number of reddened parts on the skin of the respective area on the 28$^{th}$ day after start of administration of the gel
L=number of reddened parts on the skin of the respective area before administration of the gel The data thus obtained were analyzed according to the procedure described in section 1 of the General Procedures.

Figure 6:
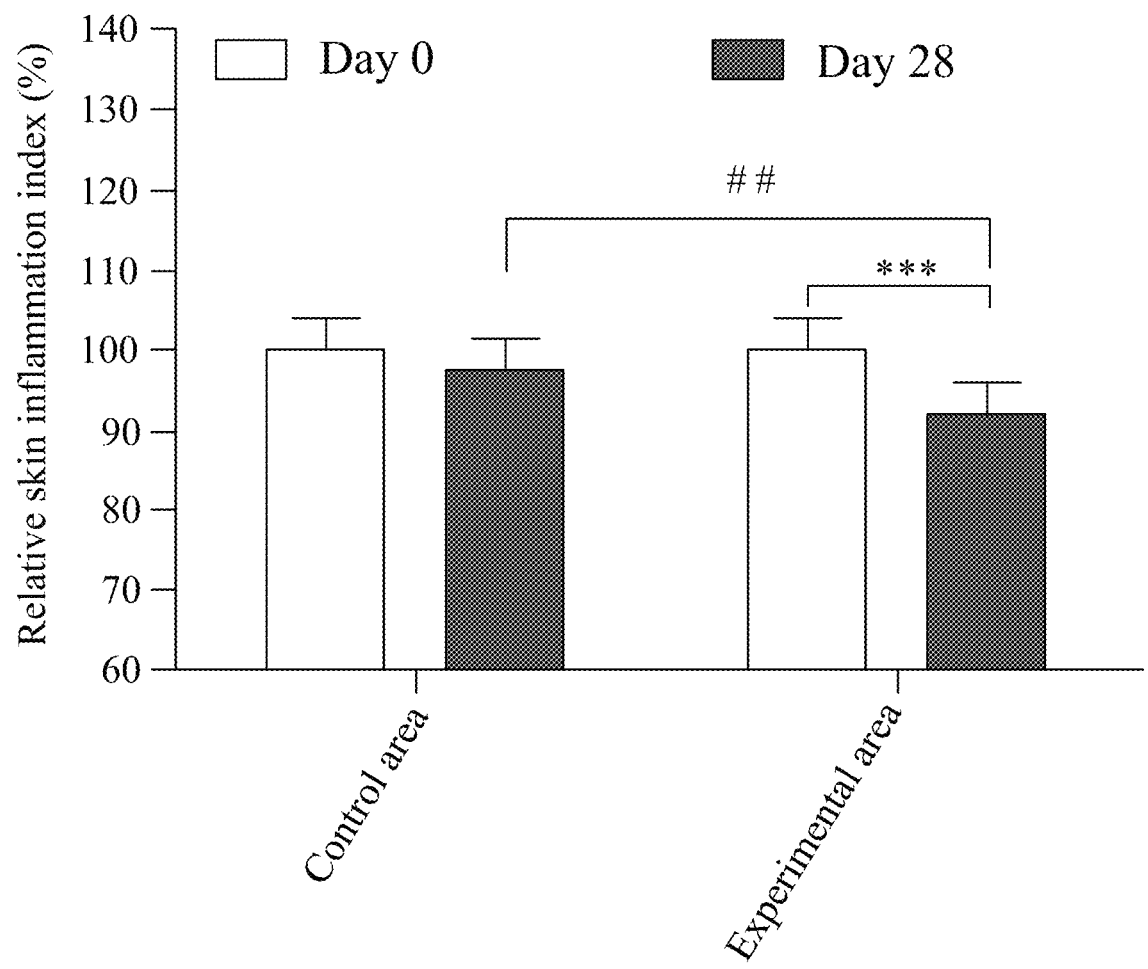
FIG. 6 shows the relative skin inflammation index in the experimental area and control area of Example 5, infra, in which the symbol "*" represents $p<0.001$ compared with the experimental area on day 0, and the symbol "##" represents $p<0.01$ compared with the control area on day 28 after start of administration.

FIG. 6 shows the relative skin inflammation index in the experimental area and the control area respectively administered with the experimental gel and the control gel, before administration (i.e., on day 0) and on day 28 after start of administration. As shown in FIG. 6, after 28 days of administration of the gel, the relative skin inflammation index determined in the control area exhibited no significant change, while the relative skin inflammation index determined in the experimental area decreased significantly and was also significantly lower than that in the control area.

D. Determination of Relative Amount of Skin Brown Spots

Before administration of the gel (i.e., on day 0), and on the 28$^{th}$ day after start of administration of the gel, for each test subject, the skin of the experimental area administered with the experimental gel and the skin of the control area administered with the control gel were subjected to measurement of the number of skin brown spots using VISIA™ Complexion Analysis (Manufacturer: Canfield Scientific, Inc., USA).

The relative amount of skin brown spots was calculated by substituting the number of skin brown spots on the respective one of the experimental and control areas on day 0 and on the 28$^{th}$ day after start of administration of the gel into the following formula (5):

$$M=(N/O)\times 100 \quad (5)$$

where M=relative amount of skin brown spots (%)
N=number of skin brown spots on the respective area on the 28$^{th}$ day after start of administration of the gel
O=number of skin brown spots on the respective area before administration of the gel The data thus obtained were analyzed according to the procedure described in section 1 of the General Procedures.

Figure 7:
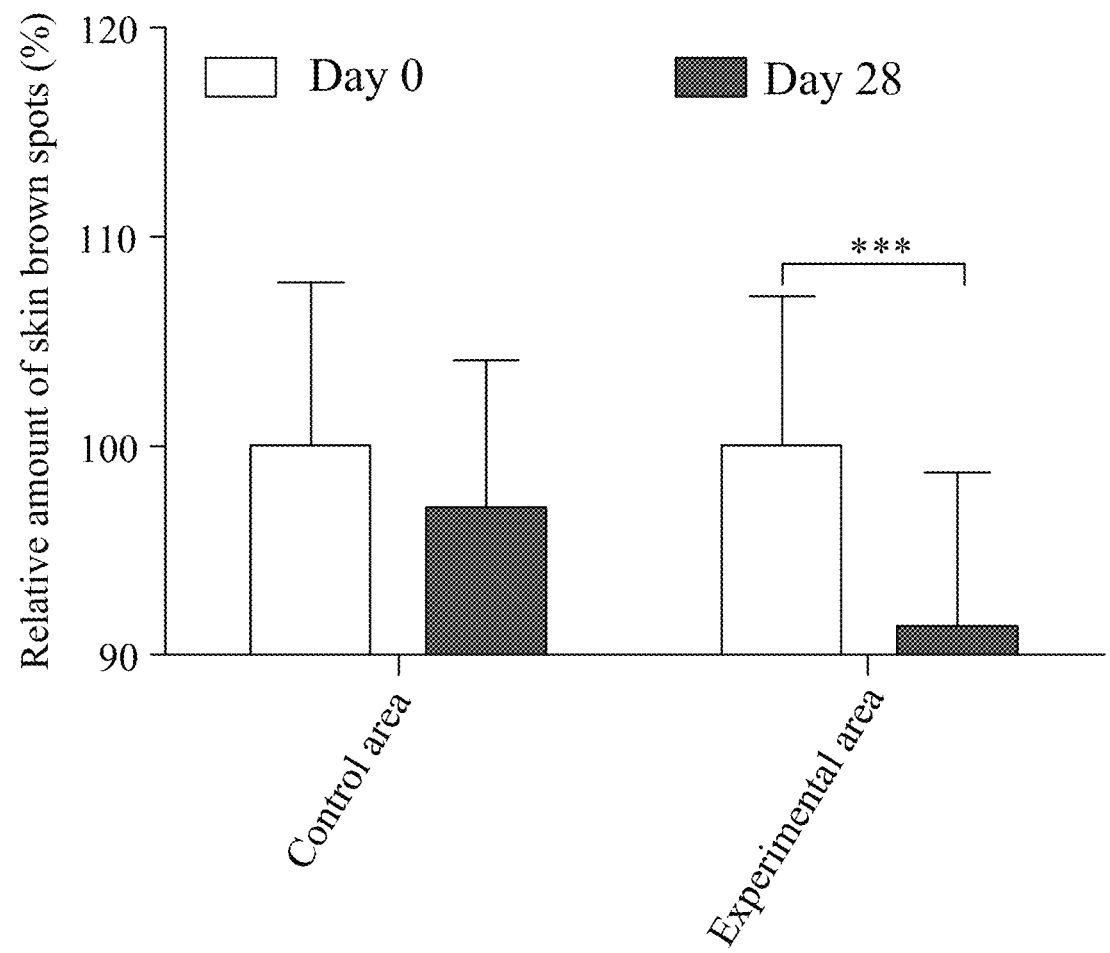
FIG. 7 shows the relative amount of skin brown spots in the experimental area and control area of Example 5, infra, in which the symbol "*" represents $p<0.001$ compared with the experimental area on day 0.

FIG. 7 shows the relative amount of skin brown spots in the experimental area and the control area respectively administered with the experimental gel and the control gel, before administration (i.e., on day 0) and on day 28 after start of administration. As shown in FIG. 7, after 28 days of administration of the gel, the relative amount of skin brown spots determined in the experimental area was significantly reduced, while that determined in the control area exhibited no significant change.

These results indicate that the three-probiotic culture supernatant C2, which was prepared by cultivating, in a collagen solution, the probiotic inoculums of Lactobacillus acidophilus TYCA06, Lactobacillus salivarius subsp. salicinius AP-32, and Bifidobacterium animalis subsp. lactis CP-9 in a number ratio of 1:1:1, is capable of effectively treating acne, reducing skin inflammation, and reducing formation of skin brown spots.

Taken together, the aforesaid results suggest that the probiotic culture of the present disclosure, which is prepared by cultivating in a collagen solution, Lactobacillus acidophilus TYCA06, Lactobacillus salivarius subsp. salicinius AP-32, and Bifidobacterium animalis subsp. lactis CP-9 in a number ratio ranging from 1:0.125:0.125 to 1:8:8, has an excellent antibacterial activity (especially against skin pathogens), and is capable of promoting wound healing, inhibiting melanogenesis, and improving various skin conditions. Therefore, the probiotic culture of the present disclosure is believed to have a high potential to be developed as topical medicaments for skin conditions and skin care products.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A probiotic culture, comprising a probiotic mixture in a collagen solution,
   wherein the probiotic mixture includes Lactobacillus acidophilus TYCA06 which is deposited at the China General Microbiological Culture Collection Center (CGMCC) under an accession number CGMCC 15210, Lactobacillus salivarius subsp. salicinius AP-32 which is deposited at the China Center for Type Culture Collection (CCTCC) under an accession number CCTCC M 2011127, and Bifidobacterium animalis subsp. lactis CP-9 which is deposited at the CCTCC under an accession number CCTCC M 2014588, and a ratio of colony forming units of Lactobacillus acidophilus TYCA06, Lactobacillus salivarius subsp. salicinius AP-32, and Bifidobacterium animalis subsp. lactis CP-9 ranges from 1:0.125:0.125 to 1:8:8.

2. The probiotic culture as claimed in claim 1, wherein the ratio of colony forming units of Lactobacillus acidophilus TYCA06, to Lactobacillus salivarius subsp. salicinius AP-32, and to Bifidobacterium animalis subsp. lactis CP-9 in the probiotic mixture is 1:1:1.

3. A method for improving a skin condition, comprising administering to a subject in need thereof a composition including a probiotic culture as claimed in claim 1.

4. The method as claimed in claim 3, wherein the skin condition is selected from the group consisting of wound, melanogenesis, acne, skin inflammation, skin brown spots, skin pathogen infection, and combinations thereof.

5. The method as claimed in claim 3, wherein the composition is formulated as a pharmaceutical composition or a cosmeceutical composition.

6. The method as claimed in claim 5, wherein the pharmaceutical composition is in a dosage form for oral administration.

7. A method for inhibiting pathogenic infection, comprising administering to a subject in need thereof a composition including a probiotic culture as claimed in claim 1.

8. The method as claimed in claim 7, wherein the pathogenic infection is caused by a pathogen selected from the group consisting of *Staphylococcus aureus, Propionibacterium acnes, Escherichia coli, Gardnerella vaginalis, Epidermophyton floccosum, Trichophyton rubrum*, and combinations thereof.

9. The method as claimed in claim 7, wherein the composition is formulated as a pharmaceutical composition or a cosmeceutical composition.

10. The method as claimed in claim 9, wherein the pharmaceutical composition is in a dosage form for oral administration.

11. A method for improving a skin condition, comprising administering to a subject in need thereof a composition including a probiotic culture comprising a probiotic mixture, wherein the probiotic culture is prepared by cultivating the probiotic mixture in a collagen solution, wherein the probiotic mixture includes *Lactobacillus acidophilus* TYCA06 which is deposited at the China General Microbiological Culture Collection Center (CGMCC) under an accession number CGMCC 15210, *Lactobacillus salivarius* subsp. *salicinius* AP-32 which is deposited at the China Center for Type Culture Collection (CCTCC) under an accession number CCTCC M 2011127, and *Bifidobacterium animalis* subsp. *lactis* CP-9 which is deposited at the CCTCC under an accession number CCTCC M 2014588, and a ratio of colony forming units of *Lactobacillus acidophilus* TYCA06, *Lactobacillus salivarius* subsp. *salicinius* AP-32, and *Bifidobacterium animalis* subsp. *lactis* CP-9 ranges from 1:0.125:0.125 to 1:8:8.

12. The method as claimed in claim 11, wherein the skin condition is selected from the group consisting of wound, melanogenesis, acne, skin inflammation, skin brown spots, skin pathogen infection, and combinations thereof.

13. The method as claimed in claim 11, wherein the composition is formulated as a pharmaceutical composition or a cosmeceutical composition.

14. The method as claimed in claim 13, wherein the pharmaceutical composition is in a dosage form for oral administration.

15. A method for inhibiting pathogenic infection, comprising administering to a subject in need thereof a composition including a probiotic culture comprising a probiotic mixture, wherein the probiotic culture is prepared by cultivating the probiotic mixture in a collagen solution, wherein the probiotic mixture includes *Lactobacillus acidophilus* TYCA06 which is deposited at the China General Microbiological Culture Collection Center (CGMCC) under an accession number CGMCC 15210, *Lactobacillus salivarius* subsp. *salicinius* AP-32 which is deposited at the China Center for Type Culture Collection (CCTCC) under an accession number CCTCC M 2011127, and *Bifidobacterium animalis* subsp. *lactis* CP-9 which is deposited at the CCTCC under an accession number CCTCC M 2014588, and a ratio of colony forming units of *Lactobacillus acidophilus* TYCA06, *Lactobacillus salivarius* subsp. *salicinius* AP-32, and *Bifidobacterium animalis* subsp. *lactis* CP-9 ranges from 1:0.125:0.125 to 1:8:8.

16. The method as claimed in claim 15, wherein the pathogenic infection is caused by a pathogen selected from the group consisting of *Staphylococcus aureus, Propionibacterium acnes, Escherichia coli, Gardnerella vaginalis, Epidermophyton floccosum, Trichophyton rubrum*, and combinations thereof.

17. The method as claimed in claim 15, wherein the composition is formulated as a pharmaceutical composition or a cosmeceutical composition.

18. The method as claimed in claim 17, wherein the pharmaceutical composition is in a dosage form for oral administration.

* * * * *